United States Patent
Li et al.

(10) Patent No.: US 12,234,482 B2
(45) Date of Patent: Feb. 25, 2025

(54) CULTURE MEDIUM FOR EXPANDING AND CULTURING HUMAN LIVER PROGENITOR CELLS AND APPLICATION THEREOF

(71) Applicant: Guangzhou Institutes of Biomedicine and Health, Chinese Academy of Sciences, Guangzhou (CN)

(72) Inventors: Yinxiong Li, Guangzhou (CN); Tingcai Pan, Guangzhou (CN); Yan Chen, Guangzhou (CN); Yuanqi Zhuang, Guangzhou (CN); Fan Yang, Guangzhou (CN)

(73) Assignee: GUANGZHOU INSTITUTES OF BIOMEDICINE AND HEALTH, CHINESE ACADEMY OF SCIENCES, Guangzhou (CN)

(*) Notice: Subject to any disclaimer, the term of this patent is extended or adjusted under 35 U.S.C. 154(b) by 834 days.

(21) Appl. No.: 17/310,193

(22) PCT Filed: Dec. 19, 2019

(86) PCT No.: PCT/CN2019/126578
§ 371 (c)(1),
(2) Date: Jul. 26, 2021

(87) PCT Pub. No.: WO2020/151418
PCT Pub. Date: Jul. 30, 2020

(65) Prior Publication Data
US 2022/0186181 A1 Jun. 16, 2022

(30) Foreign Application Priority Data
Jan. 25, 2019 (CN) .......................... 201910073515.7

(51) Int. Cl.
C12N 5/071 (2010.01)

(52) U.S. Cl.
CPC .......... *C12N 5/067* (2013.01); *C12N 2500/25* (2013.01); *C12N 2501/11* (2013.01);
(Continued)

(58) Field of Classification Search
CPC ........................................... C12N 5/067
See application file for complete search history.

(56) References Cited

U.S. PATENT DOCUMENTS

2014/0308743 A1 10/2014 Riken

FOREIGN PATENT DOCUMENTS

| CN | 103800895 | 5/2014 |
| CN | 104388383 | 3/2015 |

(Continued)

OTHER PUBLICATIONS

English machine translation of Yan et al., CN 106754636 A, 2017.*
(Continued)

*Primary Examiner* — Rosanne Kosson
(74) *Attorney, Agent, or Firm* — Woodard, Emhardt, Henry, Reeves & Wagner, LLP

(57) ABSTRACT

Provided are a culture medium for expanding and cultivating human liver progenitor cells and an application thereof. The chemical components of the formula of the described culture medium are clear, no serum is present, and various components thereof cooperate with each other to synergize. The culture medium is used for the long-term expansion and cultivation of liver progenitor cells in vitro and is used for maintaining the dryness thereof, is beneficial in quickly and efficiently obtaining a large number of functional liver cells, and is suitable for clinical hepatocyte transplantation application as well as for the use of hepatocyte reactors in bioartificial livers.

16 Claims, 15 Drawing Sheets

(52) U.S. Cl.
CPC ...... *C12N 2501/12* (2013.01); *C12N 2501/15* (2013.01); *C12N 2501/155* (2013.01); *C12N 2501/41* (2013.01); *C12N 2501/73* (2013.01)

(56) References Cited

FOREIGN PATENT DOCUMENTS

| CN | 104428410 | 3/2015 | | |
|----|-----------|--------|---|---|
| CN | 106566799 | 4/2017 | | |
| CN | 106754636 | 5/2017 | | |
| WO | WO 2012/168930 | 12/2012 | | |
| WO | WO 2014/044646 | 3/2014 | | |
| WO | WO 2015173425 | 11/2015 | | |
| WO | WO 2018/128779 | 7/2018 | | |
| WO | WO-2018154329 A1 | * | 8/2018 | ............. C12N 5/073 |

OTHER PUBLICATIONS

English machine translation of Li et al., CN 104388383 B, 2017.*
Lian et al. "Hedgehog Signaling Pathway and Liver Injury: Potential Targets for Drug Action" Chinese Pharmacological Bulletin, Apr. 2014. pp. 460-464.
Tingcai Pan et al. "Robust Expansion and Functional Maturation of Human Hepatoblasts by Chemical Strategy" Stem Cell research & Therapy, 12:151 (2021), pp. 2-13.
Xiang et al. "Several Aspects of Liver Stem Cell Biology" Chinese Bulletin of Life Sciences, vol. 21, No. 5, Oct. 2009.
Extended Search Report in related EP19912048 mailed Sep. 30, 2022.
Muzi et al. "Generation of Self-Renewing Hepatoblasts from Human Emryonic Stem Cells by Chemical Approaches", Stem Cells Translational Medicine, vol. 4, No. 11, pp. 1275-1282.
Xing et al. "Signaling cross-talk between TGF-&/BMP and other pathways", Cell Research, vol. 19, No. 1, pp. 71-88.
Hirose, Y. et al "Hedgehog Signal Activation Coordinates Proliferation and Differentiation of Fetal Liver Progenitor Cells" Experimental Cell Research, vol. 315, No. 15, Jun. 24, 2009.
International Search Report of PCT/CN2019/126578 mailed Feb. 6, 2020.
Lv, L.J et al. "Self-Renewal of Hepatoblasts Under Chemically Defined Conditions by Iterative Growth Factor and Chemical Screening" Hepatology, vol. 61, No. 1, Jan. 31, 2015.
Pan, T.C. et al. "Synergistic Modulation of Signaling Pathways to Expand and Maintain the Bipotency of Human Hepatoblasts" Stem Cell Research & Therapy, vol. 10, Dec. 2, 2019, art. 364.
Touboul, T. et al "Stage-specific Regulation of the WNT/B-catenin Pathway Results in Improved Differentiation of hESCs to Functional Hepatocytes" Journal of Hepatology, vol. 64, No. 6, Feb. 26, 2016.
Zhang, M. Z. et al. "Generation of Self- Renewing Hepatoblasts From Human Embryonic Stem Cells by Chemical Approaches" Stem Cells Translational Medicine, vol. 4, No. 11, Sep. 14, 2015.

* cited by examiner

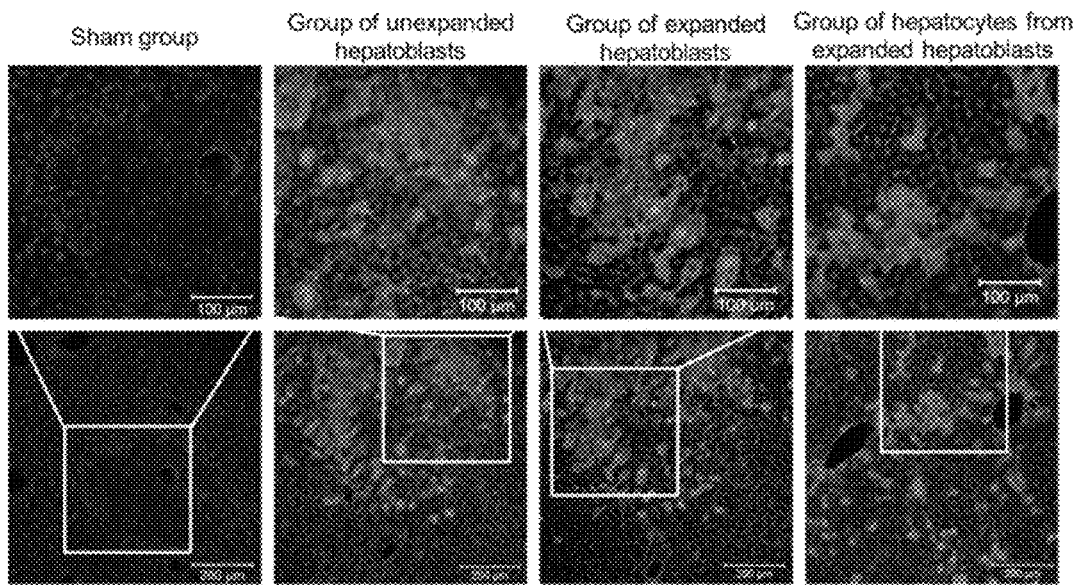
Figure 5D
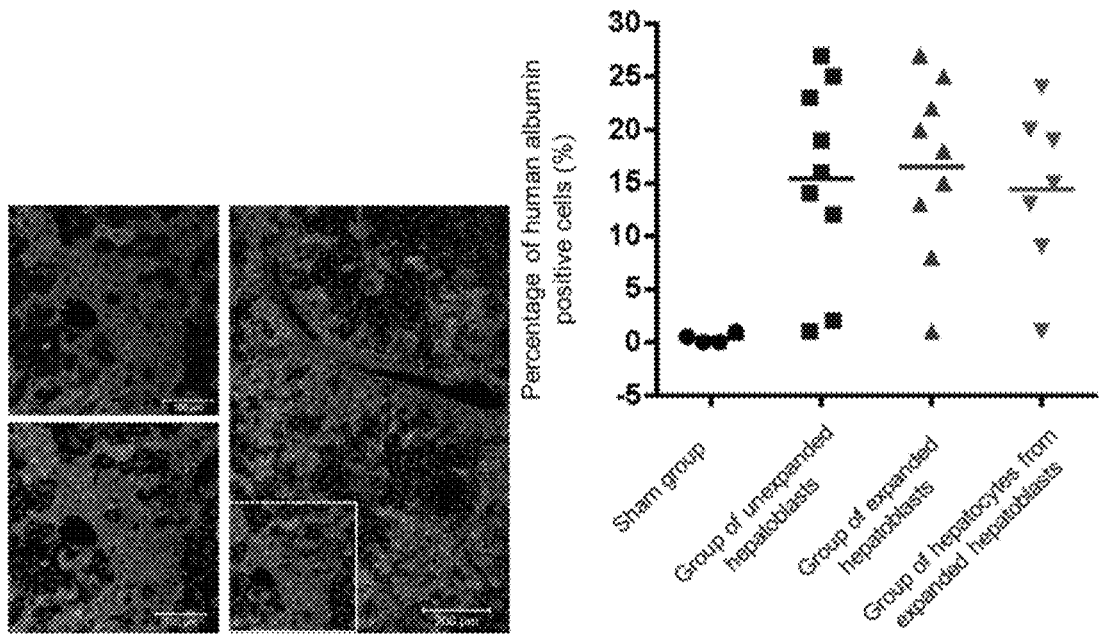
Figure 5E
Figure 5F

CULTURE MEDIUM FOR EXPANDING AND CULTURING HUMAN LIVER PROGENITOR CELLS AND APPLICATION THEREOF

TECHNICAL FIELD

The present application relates to the technical field of bioengineering and, in particular, to a culture medium for expanding and culturing human hepatoblasts and use thereof.

BACKGROUND

There are a huge number of liver diseases in China. More than 100 million people suffer from various liver diseases such as viral hepatitis, fatty liver and liver fibrosis, and about 30 million chronic hepatitis patients are people at high risk, some of which progressively develop into severe liver diseases such as liver fibrosis, liver cirrhosis, liver failure and liver cancer. Every year, more than 1 million new cases enter a decompensation period of liver cirrhosis, about 500 thousand people die of liver failure, and thousands of people die of liver failure caused by food- or drug-induced liver poisoning. Liver diseases due to various factors cause huge social and family burdens.

Liver transplantation is the only effective treatment for liver failure. In China, every year more than 500 thousand patients wait for liver transplantation while several hundreds to about one thousand liver sources can be used for liver transplantation. The limited number of liver sources is far from meeting a huge and urgent clinical requirement. Existing clinical treatments and preclinical researches have shown that both bioartificial liver dialysis and hepatocyte transplantation contribute to the improvement of livers and general microenvironments and physiological conditions and contribute to liver repair and the recovery of liver functions. This might salvage toxic acute liver failure and, more importantly, can delay or prevent the progression of some patients with advanced liver diseases into end-stage liver failure. Both treatments require a large number of hepatocytes. Human primary hepatocytes are ideal seed cells and mainly obtained from livers that are not suitable for liver transplantation. However, primary hepatocytes cannot be cultured and expanded in vitro and a source thereof is limited by the shortage of liver-derived donors. In recent years, the frontier cognition of researches on stem cells and the emergence of new technologies bring new opportunities for this breakthrough. Human pluripotent stem cells (hPSCs), including human embryonic stem cells (ESCs) and human induced pluripotent stem cells (iPSCs), have a good capability of self-proliferation and the potential of multipotent differentiation. hPSCs can be induced in theory to differentiate into all types of human cells including mature hepatocytes. The directed differentiation of hPSCs to liver lineage is to stimulate the development of liver in vivo. The hPSCs are induced into definitive endoderm cells, hepatoblasts (HBs) and mature hepatocytes in sequence. There are still some difficulties in preparing large amounts of liver donor cells from hPSCs for clinical applications. Main problems are the low efficiency in inducing hPSCs to differentiate to liver lineage and a difficulty in maintaining the extensive culture and expansion of the obtained hepatocytes in vitro. Especially for the latter, a large number of hepatocytes required are difficult to be acquired. For the clinical treatment of liver diseases though hepatocyte transplantation, $10^9$ hepatocytes are expected to be required per transplant and more hepatocytes are required to be applied to bioartificial liver and drug development. Therefore, it is of great significance to acquire a large number of functional hepatocytes quickly and efficiently and apply them to the treatment of liver diseases such as cell transplantation and bioartificial liver dialysis.

Under in vitro culture conditions, mature hepatocytes are difficult to grow and expand for a long term and maintain their intrinsic cellular characteristics. Compared with mature hepatocytes, HBs have a strong capability of proliferation and the dual potential to rapidly differentiate into hepatocytes and cholangiocytes. Therefore, the large-scale expansion of HBs derived from hPSC-induced differentiation enables the HBs to rapidly and stably proliferate and maintain a good differentiation state, which is an ideal method for acquiring a large number of functional hepatocytes. On one hand, HBs can be cryopreserved to establish an HB bank so that a large number of seed cells can be quickly and efficiently acquired. On the other hand, HBs can further be rapidly induced to differentiate into mature hepatocytes or cholangiocytes. This method can provide feasible technical support for the establishment of a liver cell bank.

In recent years, the studies on the expansion of HBs have been reported by several laboratories. However, it was reported in most of these studies that a few kinds of marker proteins of HBs were used for evaluating the dual potential of the expanded HBs and many relevant cell function evaluations were lacking. In addition, trophoblast cells or additives with unclear components such as fetal bovine serum were used in the culture conditions of some methods for expanding HBs. However, when the hepatocytes to be used for cell therapy are contaminated with animal serum, proteins or other cells, acute immune rejection and potential infections by animal viruses are often caused in clinical applications. Therefore, the hepatocytes cultured and acquired in this manner are unsuitable for clinical applications. This is also a factor to be taken into consideration when HBs are expanded and cultured in vitro.

At present, an effective method for long-term culturing and expanding HBs in vitro has not been established in the industry. Difficulties lie in the lack of a deep understanding of the process and regulation mechanism of the differentiation of hPSCs into liver cells and the unclear regulation mechanisms of HB proliferation and sternness maintenance.

Therefore, elucidating the regulation mechanism during directed differentiation of hPSCs to liver lineage, clarifying the regulation mechanism during HB proliferation and sternness maintenance, and establishing a method for expanding and culturing HBs with a formula having clear chemical components and being serum-free so as to expand and culture HBs in a large scale will facilitate the rapid and efficient acquisition of a large number of functional hepatocytes, which may be used in the treatment of liver diseases such as cell transplantation and bioartificial liver dialysis, and thus has a broad application prospect and a huge market value.

SUMMARY

The following is a summary of the subject matter described in detail herein. This summary is not intended to limit the scope of the claims.

The present application provides a culture medium for expanding and culturing human hepatoblasts and use thereof. The culture medium has clear chemical components which cooperate with each other for synergy. The culture medium is used for expanding and culturing human hepatoblasts in vitro and maintaining sternness of the human hepatoblasts, and has a broad application prospect and a huge market value.

To achieve the object, the present application adopts technical solutions described below.

In a first aspect, the present application provides a culture medium for expanding and culturing human hepatoblasts, comprising a liquid basal culture medium, an insulin-transferrin-sodium selenite mixture, a cytokine, a glycogen synthase kinase 3β inhibitor, a Hedgehog signaling pathway activator, and a transforming growth factor β receptor inhibitor.

Preferably, the culture medium further includes albumin.

In the present application, based on an established method for inducing directed differentiation to liver lineage, the inventors have, in a long-term scientific research process, analyzed signaling pathways related to proliferation and differentiation of HBs, clarified the regulation mechanisms of key signaling pathways such as Wnt, TGF-β, BMP, and Hedgehog on HB proliferation and maintenance of liver progenitor characteristics, and further adopted cytokines and small molecule compounds to regulate related signaling pathways and fully screened active components to develop the formula of the culture medium which supports stable proliferation of HBs and better maintains the liver progenitor characteristics. Components and conditions in the culture medium cooperate with each other for synergy. HBs obtained through large-scale culture and expansion can better maintain the characteristics of HBs comprising the ability to directly and rapidly differentiate into functional mature hepatocytes or cholangiocytes, which, when transplanted into liver injury model mice, may be homed and colonized into liver tissues, proliferate and further differentiate into hepatocytes expressing human ALB and cholangiocytes expressing human CK19, participate in the repair of liver parenchyma and the reconstruction of bile ducts, effectively recover the function of injured liver, and save liver injury model animals.

Preferably, the liquid basal culture medium includes any one or a combination of at least two of a cell culture medium RMPI1640, a cell culture medium DMEM/F12, a cell culture medium MEM, a cell culture medium DMEM, a cell culture medium IMDM, a cell culture medium 199, or a cell culture medium F10.

Preferably, the albumin includes human recombinant albumin and/or bovine serum albumin.

Preferably, the albumin has a mass concentration of 5 µg/mL to 500 µg/mL, which may be, for example, 5 µg/mL, 20 µg/mL, 40 µg/mL, 60 µg/mL, 80 µg/mL, 100 µg/mL, 200 µg/mL, 300 µg/mL, 400 µg/mL, or 500 µg/mL.

Preferably, the cytokine includes a bone morphogenetic growth factor, hepatocyte growth factor, and epidermal growth factor.

Preferably, the bone morphogenetic growth factor includes BMP2 and/or BMP4.

Preferably, the bone morphogenetic growth factor has a mass concentration of 1 ng/mL to 50 ng/mL, which may be, for example, 1 ng/mL, 5 ng/mL, 10 ng/mL, 15 ng/mL, 20 ng/mL, 25 ng/mL, 30 ng/mL, 35 ng/mL, 40 ng/mL, 45 ng/mL, or 50 ng/mL.

Preferably, the hepatocyte growth factor has a mass concentration of 1 ng/mL to 100 ng/mL, which may be, for example, 1 ng/mL, 10 ng/mL, 20 ng/mL, 30 ng/mL, 40 ng/mL, 50 ng/mL, 60 ng/mL, 70 ng/mL, 80 ng/mL, 90 ng/mL, or 100 ng/mL.

Preferably, the epidermal growth factor has a mass concentration of 1 ng/mL to 200 ng/mL, which may be, for example, 1 ng/mL, 10 ng/mL, 20 ng/mL, 30 ng/mL, 40 ng/mL, 50 ng/mL, 60 ng/mL, 70 ng/mL, 80 ng/mL, 90 ng/mL, 100 ng/mL, 120 ng/mL, 140 ng/mL, 160 ng/mL, 180 ng/mL, or 200 ng/mL.

Preferably, the insulin-transferrin-sodium selenite mixture has a volume percent content of 0.10% to 10%, which may be, for example, 0.1%, 0.2%, 0.4%, 0.5%, 0.6%, 0.8%, 1%, 2%, 3%, 4%, 5%, 6%, 7%, 8%, 9%, or 10%.

Preferably, the glycogen synthase kinase 3β inhibitor includes CHIR99021 and/or CHIR98014.

Preferably, the glycogen synthase kinase 3β inhibitor has a molar concentration of 10 nM to 100 µM, which may be, for example, 10 nM, 100 nM, 30 µM, 40 µM, 50 µM, 60 µM, 70 µM, 80 µM, 90 µM, or 100 µM.

Preferably, the transforming growth factor β receptor inhibitor includes any one or a combination of at least two of A8301, SB431542, or E-616452.

Preferably, the transforming growth factor β receptor inhibitor has a molar concentration of 50 nM to 50 µM, which may be, for example, 50 nM, 100 nM, 10 µM, 20 µM, 30 µM, 40 µM, or 50 µM.

Preferably, the Hedgehog signaling pathway activator includes SAG and/or Purmorphaminede.

Preferably, the Hedgehog signaling pathway activator has a molar concentration of 10 nM to 50 µM, which may be, for example, 10 nM, 100 nM, 10 µM, 20 µM, 30 µM, 40 µM, or 50 µM.

The GSK3β inhibitor may be CHIR99021 or other GSK3β inhibitors in form of small molecules or proteins.

The TGF-β receptor inhibitor may be A8301, SB431542, and E-616452, or other TGF-β receptor inhibitors.

The Hedgehog signaling pathway activator may be SAG or other Hedgehog signaling pathway activators such as Purmorphaminede.

Specifically, the culture medium includes a liquid basal culture medium, 5 µg/mL to 500 µg/mL of human recombinant albumin or bovine serum albumin, 0.10% to 10% (volume percent content) of an insulin-transferrin-sodium selenite (ITS) mixture; 10 nM to 10 µM of a glycogen synthase kinase 3β (GSK3β) inhibitor, 50 nM to 50 µM of a transforming growth factor β (TGF-β) receptor inhibitor, 1 ng/mL to 50 ng/mL of a bone morphogenetic growth factor (BMP2 or BMP4), 1 ng/mL to 100 ng/mL of hepatocyte growth factor (HGF), 1 ng/mL to 200 ng/mL of epidermal growth factor (EGF), and 10 nM to 50 µM of a Hedgehog signaling pathway activator.

In a second aspect, the present application provides a method for expanding and culturing human hepatoblasts (HBs) in vitro for a long term using the culture medium in the first aspect.

Preferably, the method includes steps as follows:
(1) obtaining Ep-CAM$^+$/C-kit$^-$ HBs; and
(2) subculturing the cells obtained in step (1) in vitro by using the culture medium in the first aspect;

Preferably, the HBs in step (1) are from a source comprising any one or a combination of at least two of human pluripotent stem cells (hPSCs), hepatic stem cells, hepatoblasts or oval cells.

The HBs in step (1) include HBs obtained by inducing differentiation of human pluripotent stem cells (hPSCs), and HBs from other sources, including hepatic stem cells, hepatoblasts or oval cells from human adult liver tissues.

Preferably, the HBs in step (1) are obtained by a method including flow cytometry sorting.

As a preferred technical solution, a method for expanding and culturing human hepatoblasts (HBs) in vitro for a long term specifically includes steps as follows:

(1) obtaining Ep-CAM$^+$/C-kit$^-$ HBs through flow cytometry sorting, wherein the HBs are from a source comprising any one or a combination of at least two of human pluripotent stem cells (hPSCs), hepatic stem cells, hepatoblasts, or oval cells;

(2) subculturing the cells obtained in step (1) in vitro by using the culture medium in the first aspect, to obtain a sufficient amount of HBs; and (3) further differentiating the HBs obtained in step (2) into functional mature hepatocytes or cholangiocytes.

In a third aspect, the present application provides human hepatoblasts (HBs) obtained by being expanded and cultured using the culture medium in the first aspect or using the method in the second aspect.

The HBs provided by the present application may be cultured for more than 50 passages in the culture medium, while maintaining stable HB phenotypes and related functions, comprising the ability to directly and rapidly differentiate into functional mature hepatocytes or cholangiocytes.

In a fourth aspect, the present application provide use of the HBs in the third aspect in preparation of transplanted cells for treating liver diseases, preparation of hepatocytes used in a bioartificial liver reactor, liver tissue engineering or in vitro drug screening for liver diseases.

The present application provides a system and a method for expanding and culturing HBs while maintaining stemness of the HBs in vitro for a long term, including an expansion medium with clear chemical components which is used for in vitro expansion and culture of human HBs. The present application may selectively culture and expand HBs obtained from hPSC differentiation.

Under such culture condition, HBs may be cultured and expanded in large-scale for more than 50 passages, while maintaining stable HB phenotypes comprising ability to directly and rapidly differentiate into functional mature hepatocytes or cholangiocytes. The expanded HBs, when transplanted into liver injury model mice, may be homed and colonized into liver tissues, proliferate and further differentiate into hepatocytes expressing human ALBs and cholangiocytes expressing human CK19, participate in the repair of liver parenchyma and the reconstruction of bile ducts, effectively recover the function of injured liver, and save liver injury model animals.

Compared with the related art, the present application has beneficial effects described below.

The present application provides a culture medium formula having clear chemical components and being serum-free, and a culture method, which are used for expanding and culturing HBs obtained by inducing hPSCs in vitro for a long term. This facilitates the rapid and efficient acquisition of a large number of functional hepatocytes. The HBs can be cultured for more than 50 passages under such a condition, while maintaining stable HB phenotypes and related functions comprising the ability to directly and rapidly differentiate into functional mature hepatocytes or cholangiocytes. The HBs cultured in the present application, when transplanted into the liver injury model mice, may be homed and colonized into the liver tissues, participate in the repair of liver parenchyma and the reconstruction of bile ducts, effectively recover the function of the injured liver, and save the liver injury model animals. Therefore, the present disclosure will facilitate the rapid and efficient acquisition of a large number of functional hepatocytes and is applicable to clinical hepatocyte transplantation and hepatocyte reactors in bioartificial liver.

Other aspects can be understood after the drawings and the detailed description are read and understood.

BRIEF DESCRIPTION OF DRAWINGS

FIGS. 5D to 5F are diagrams illustrating liver tissue sections for analyzing cell homing efficiency after one week of cell transplantation according to the present application;

DETAILED DESCRIPTION

To further elaborate on the technical means adopted and the effects achieved in the present application, the solutions of the present application are further described below through specific examples in conjunction with drawings, but the present application is not limited to the scope of the examples.

Example 1 Preparation of a Medium

A basal medium, i.e., RPMI1640 was supplemented with 50 μg/mL of human recombinant albumin and 1% (volume percent content) of an insulin-transferrin-sodium selenite (ITS) mixture.

HBs expansion culture media were prepared, including the above basal medium and an expansion combination: $B_{20}CEH$, $AB_{20}CEH$, $AB_{10}CEHS$, ACEHS, or ACEH. Letters in the expansion combination have the following meanings: A represents 50 nM to 50 μM of transforming growth factor β (TGF-β) receptor inhibitor A8301; $B_{10}$ or $B_{20}$ represents 10 ng/mL or 10 ng/mL of a bone morphogenetic growth factor (BMP2 or BMP4), respectively; C represents 10 nM to 10 μM of a glycogen synthase kinase 3β (GSK3β) inhibitor; E represents 1 ng/mL to 200 ng/mL of epidermal growth factor (EGF); H represents 1 ng/mL to 100 ng/mL of hepatocyte growth factor (HGF), and S represents 10 nM to 50 μM of a Hedgehog signaling pathway activator.

An optimized HBs expansion culture medium was prepared, i.e. including the above basal medium and the expansion combination $AB_{10}CEHS$, i.e. including 5 μM of A8301, 20 ng/mL of BMP4, 3 μM of CHIR99021, 20 ng/mL of EGF, 20 ng/mL of HGF, and 0.5 μM of SAG. Cells were digested with Accutase enzyme and subcultured when grown to 80% confluency.

Example 2 Expansion of HBs Obtained Through hPSC Differentiation hPSCs (H1 or iPSCs from the Key Laboratory of Stem Cells) were cultured in a 12-well plate coated with 1% Matrigel (a growth factor reduced, BD Bioscience) in culture medium mTeSR1 (Stem Cell Technologies). The culture medium was changed to a culture medium for DE-directed induction when the hPSCs grew at 60%-70% confluency, where RPMI1640 contained 2% of B27 (minus insulin, Invitrogen), 3 μM of CHIR99021 (CHIR) and 100 ng/mL of Activin A. The hPSCs were induced for one day and then induced for another two days with CHIR removed. At this time, the cells differentiated into DE cells. Then, the culture medium was changed to a culture medium for directed differentiation into hepatoblasts, where RPMI1640 contained 2% of B27 (Invitrogen), 20 ng/mL BMP2, 20 ng/mL of BMP4 and 30 ng/mL of FGF4, and the DE cells were induced for four days. The culture medium was then replaced with RPMI1640 that contained 2% of B27, 20 ng/mL of BMP4 and 20 ng/mL of HGF4 and the DE cells were induced for another three says and further differentiated into HBs.

Figure 1:
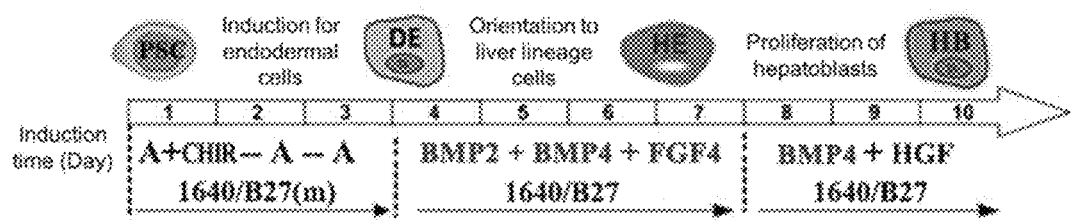
FIG. 1A is a flowchart showing directed differentiation of hPSCs to liver lineage according to the present application.
FIG. 1B illustrates changes in cell morphology during induction of HBs according to the present application.
FIG. 1C is a diagram illustrating immunofluorescence for identifying DE cells on Day 3 and HBs on Day 10 according to the present application.
FIG. 1D is a diagram illustrating flow cytometry for analyzing the expression of marker proteins and the expression of cell proliferation marker protein Ki67 at different stages of HB differentiation according to the present application.
Figure 1:
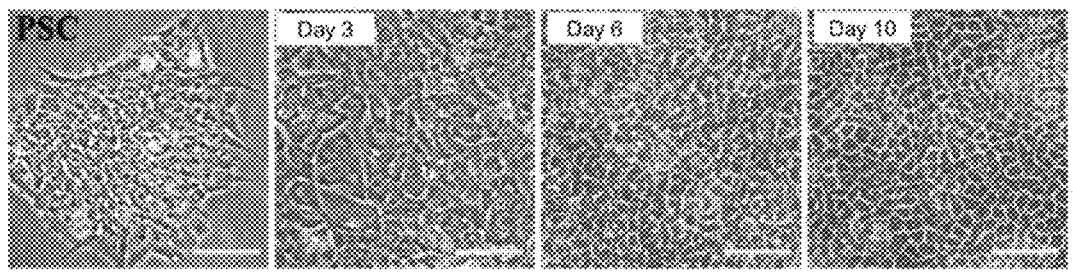
Figure 1C:
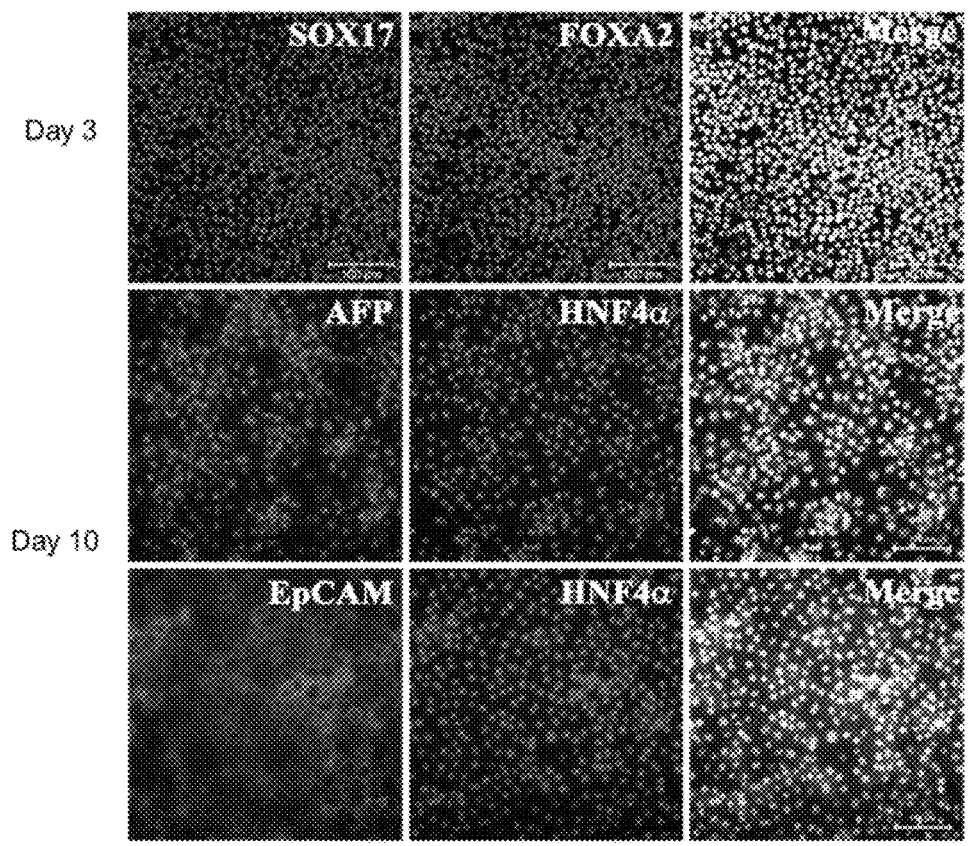
Figure 1D:
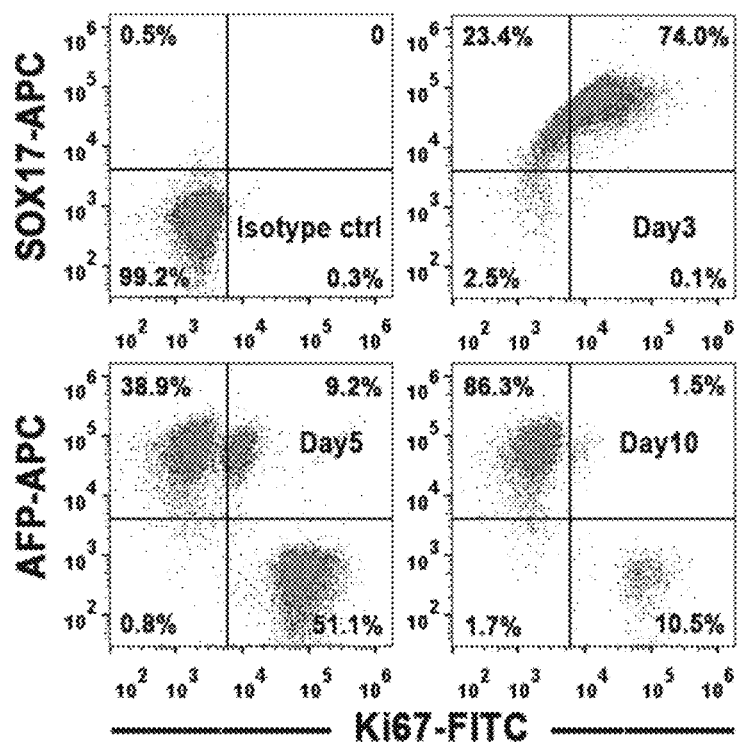

An induction process of HBs and the identification of cells at each relevant stage are shown in FIGS. 1A to 1D, wherein: a flowchart showing directed differentiation of hPSCs to liver lineage (FIG. 1A), changes in cell morphology in the induction process of HBs (FIG. 1B), immunofluorescence for identifying DE cells on Day 3 and HBs on Day 10 (FIG. 1C), and flow cytometry for analyzing the expression of marker proteins and the expression of cell proliferation marker protein Ki67 at different stages of differentiation into HBs (FIG. 1D).

hPSCs may be induced to differentiate into HBs which have a strong capability to proliferate. HBs may be expanded in large amounts under suitable culture conditions, and may further rapidly differentiate into functional mature hepatocytes and cholangiocytes. Therefore, large-scale expansion of HBs obtained through inducing hPSCs provides a source for rapid and efficient acquisition of a large number of functional hepatocytes, and thus is an effective method for meeting the requirement for a large number of hepatocytes in clinical hepatocyte transplantation and hepatocyte reactors in bioartificial liver.

At present, an effective method for long-term culturing and expanding HBs in vitro has not been established in the industry. Difficulties lie in the lack of a deep understanding of the process and regulation mechanism of the differentiation of hPSCs into liver cells and the unclear regulation mechanisms of HB proliferation and sternness maintenance. Therefore, the regulation mechanism during directed differentiation of hPSCs to liver lineage is to be elucidated, the regulation mechanism during HB proliferation and stemness maintenance is to be clarified, and a method for expanding and culturing HBs whose formula has clear chemical components and is serum-free is to be established so that HBs can be expanded and cultured to a large scale, which will facilitate the rapid and efficient acquisition of a large number of functional hepatocytes and the application of HBs to the treatment of liver diseases such as cell transplantation and bioartificial liver dialysis.

Based on an established method for inducing directed differentiation to liver lineage, signaling pathways related to proliferation and differentiation of HBs are analyzed, the regulation mechanisms of key signaling pathways such as Wnt, TGF-β, BMP, and Hedgehog on HB proliferation and maintenance of liver progenitor characteristics are clarified, and cytokines and small molecule compounds are further adopted to regulate related signaling pathways, so as to develop a formula of a culture medium which supports stable proliferation of HBs and better maintains the liver progenitor characteristics.

Figure 2A:
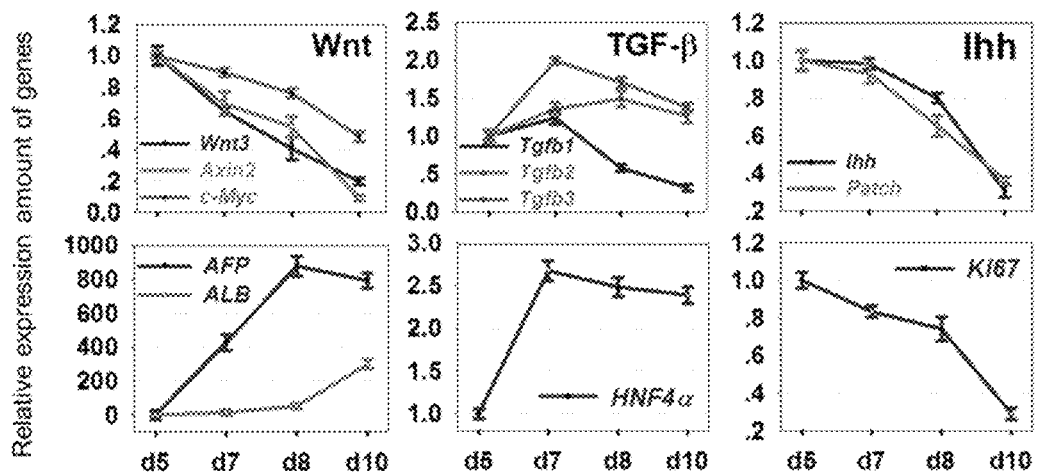
FIG. 2A is a diagram illustrating real-time polymerase chain reaction (RT-PCR) for quantitatively analyzing the activity of signaling pathways related to proliferation and differentiation of HBs according to the present application.

First, during differentiation of hPSCs into HBs, the activity of the signaling pathways related to the proliferation and differentiation of HBs was quantitatively analyzed through RT-PCR. The results showed that the activity of the signaling pathways such as Wnt or Hedgehog related to the proliferation of HBs was down-regulated during the differentiation (FIG. 2A).

Figure 2B:
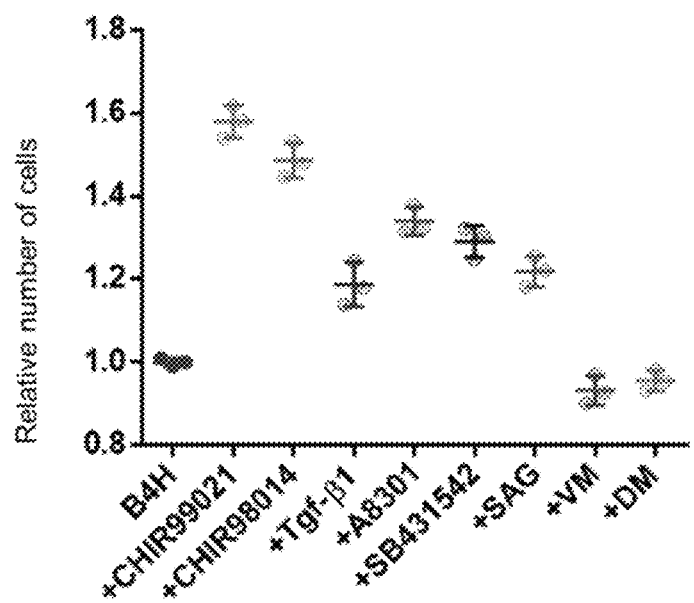
FIGS. 2B to 2D are diagrams illustrating effects of related signaling pathways regulated by small molecules on proliferation and differentiation of HBs according to the present application.
Figure 2C:
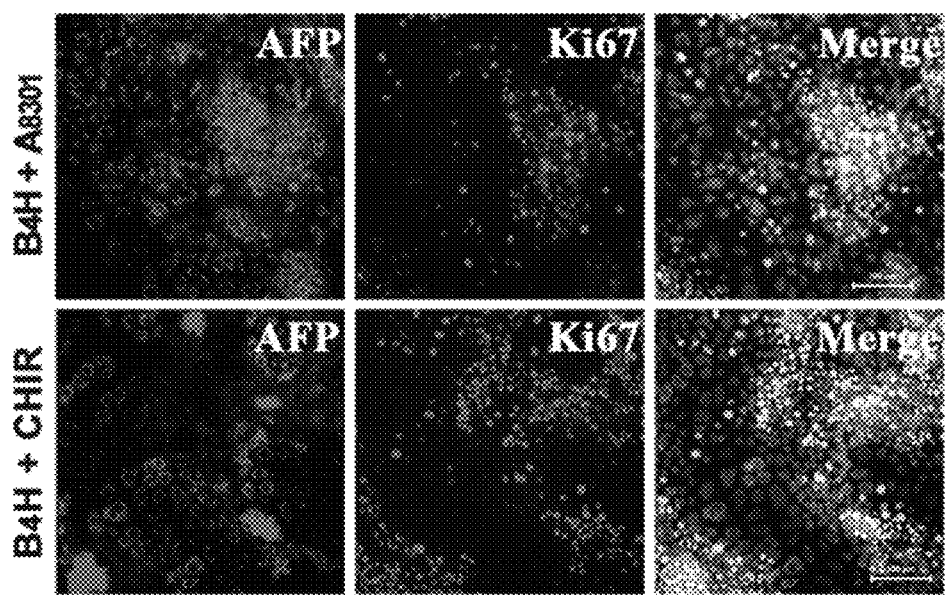

Further, effects of the signaling pathways on the proliferation and differentiation of HBs were analyzed by regulating the related signaling pathways with small molecules. The results showed that CHIR, A8301 and SAG promoted the proliferation of HBs (FIGS. 2B and 2C).

Figure 2D:
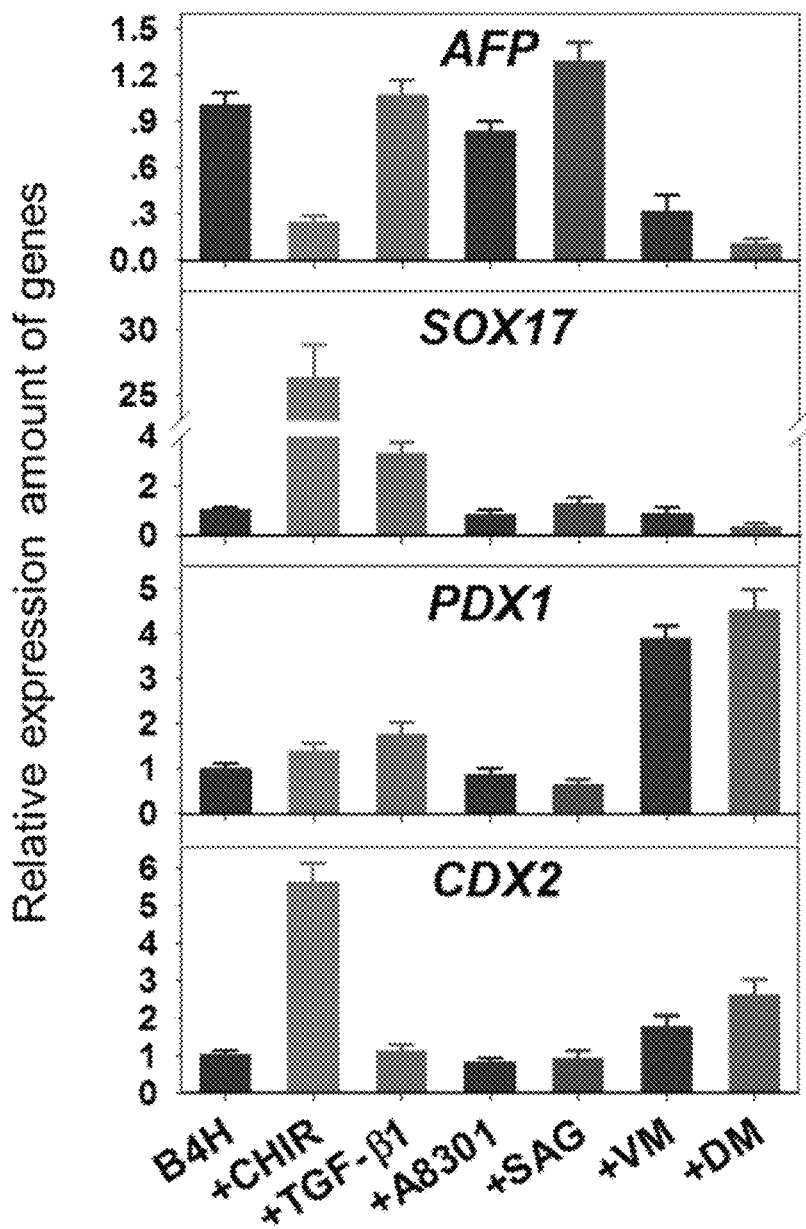

In addition to proliferation, the effects of the related signaling pathways on the characteristics of HBs were further analyzed. The results showed that CHIR promoted the proliferation of HBs and inhibited the expression of AFP, that is, inhibited the maintenance of the characteristics of HBs. Whereas, A8301 and SAG promoted the expression of liver cell-related genes such as AFP, that is, promoted the maintenance of the characteristics of HBs (FIG. 2D).

Figure 2E:
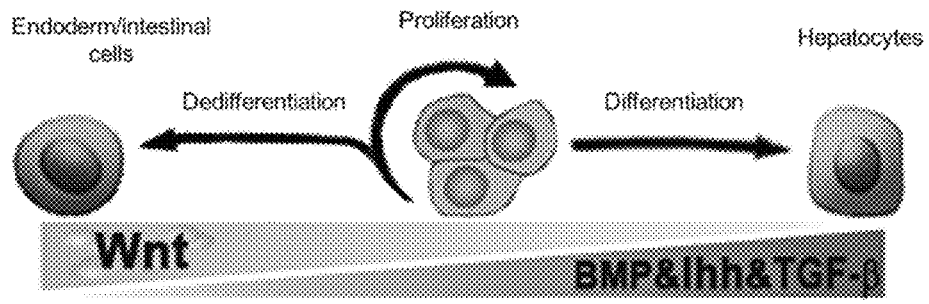
FIG. 2E is a diagram illustrating a mode in which signaling pathways regulate proliferation and differentiation of HBs according to the present application.

The above results showed the balance of the regulation of the related signaling pathways such as Wnt, TGF-β, BMP, and Hedgehog on the proliferation and differentiation of HBs (FIG. 2E).

Figure 2F:
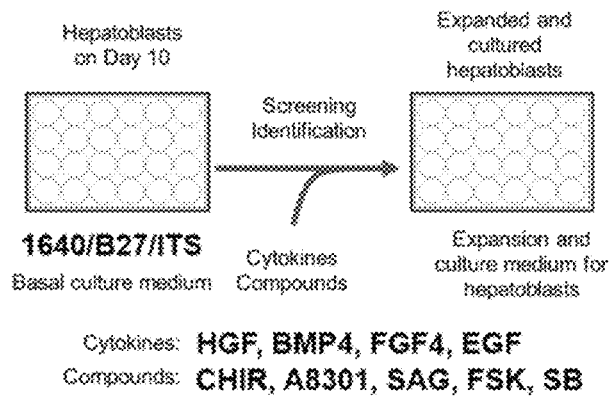
FIG. 2F is a diagram illustrating a mode in which cytokines and small molecule compounds are screened according to the present application.
Figure 2G:
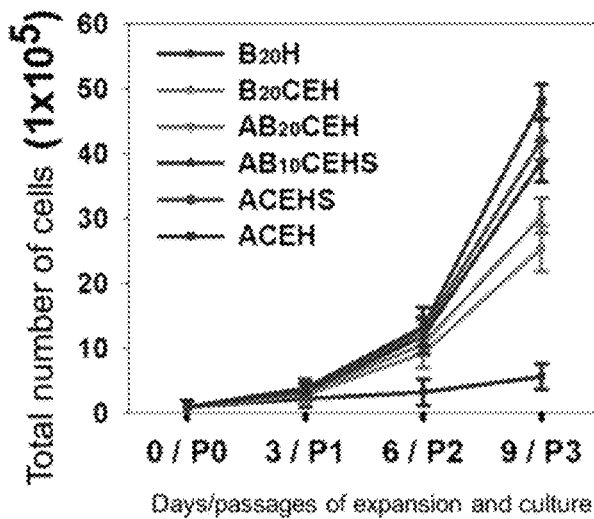
FIG. 2G is a diagram illustrating effects of different formulas of a culture medium on proliferation of HBs according to the present application.
Figure 2H:
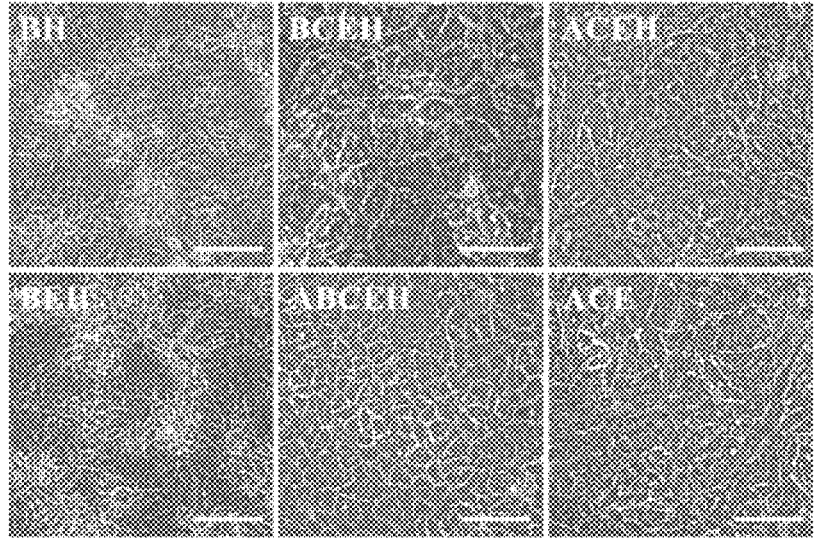
FIG. 2H is a cell morphology diagram illustrating effects of different formulas of a culture medium on proliferation of HBs according to the present application.
Figure 2I:
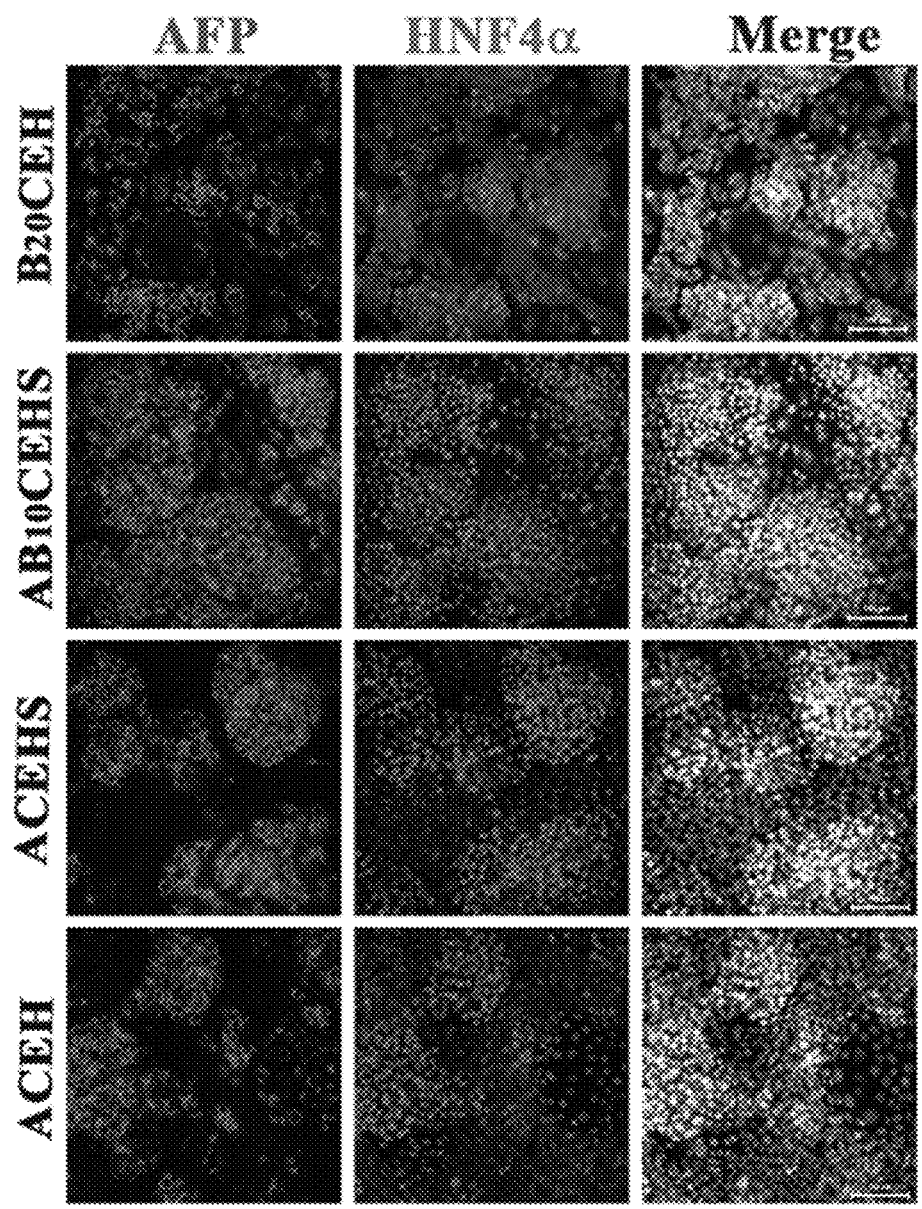
FIG. 2I is a diagram illustrating effects of different formulas of a culture medium on maintenance of characteristics of HBs according to the present application.
Figure 2J:
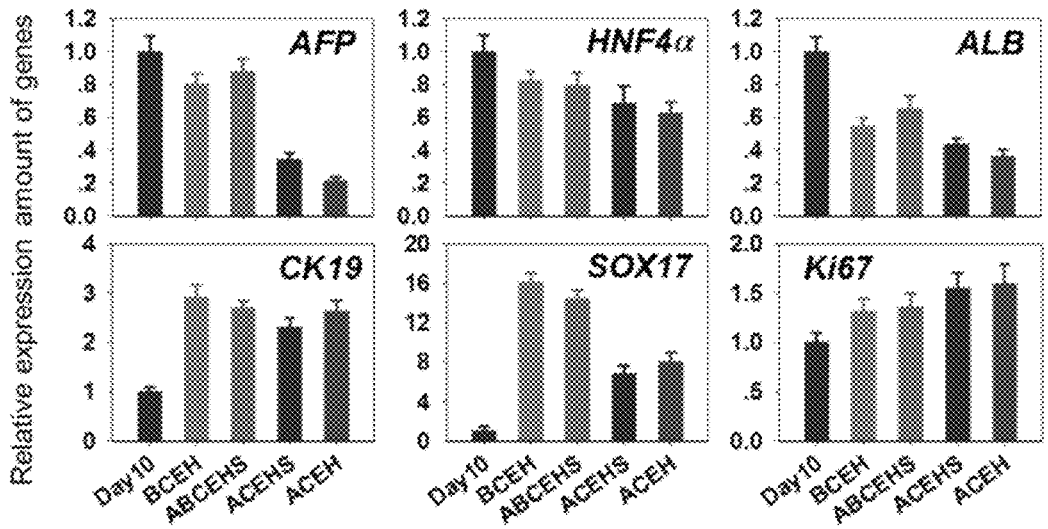
FIG. 2J is a diagram illustrating an analysis of effects of different formulas of a culture medium on expression of HB-related genes according to the present application.

Based on this, small molecule compounds were further screened to optimize the formula for the expansion and culture of HBs (FIG. 2F). It was found through expansion and culture that multiple formulas of the culture medium promoted the proliferation of HBs (FIGS. 2G and 2H). However, different formulas of the culture medium had different effects in maintaining the characteristics of HBs. The optimized formula $AB_{10}CEHS$ of the culture medium promoted the proliferation of HBs while maintaining the liver progenitor characteristics (FIGS. 2I and 2J). The effects of different formulas of the culture medium on the maintenance of the characteristics of HBs are shown in Table 1. Letters in the expansion combination have the following meanings: A represents 50 nM to 50 μM of transforming growth factor β (TGF-β) receptor inhibitor A8301; $B_{10}$ or $B_{20}$ represents 10 ng/mL or 10 ng/mL of a bone morphogenetic growth factor (BMP2 or BMP4), respectively; C represents 10 nM to 10 μM of a glycogen synthase kinase 33 (GSK3β) inhibitor; E represents 1 ng/mL to 200 ng/mL of epidermal growth factor (EGF); H represents 1 ng/mL to 100 ng/mL of hepatocyte growth factor (HGF), and S represents 10 nM to 50 μM of a Hedgehog signaling pathway activator.

TABLE 1

| Treatment | AFP$^+$ | HNF4α$^+$ |
| --- | --- | --- |
| $B_{20}$CEH | 81.8% +/− 4.2 | 83.4% +/− 4.8 |
| $AB_{20}$CEH | 94.5% +/− 3.3 | 96.2% +/− 2.3 |
| $AB_{10}$CEHS | 96.7% +/− 5.4 | 98.8% +/− 6.0 |
| ACEHS | 77.2% +/− 5.0 | 86.2% +/− 4.5 |
| ACEH | 72.7% +/− 5.2 | 81.5% +/− 6.5 |

The HBs obtained through the differentiation of hPSCs were digested into single cells by Accutase (life), resuspended in PBS containing 3% of BSA, and further incubated with Ep-CAM (Milteny) and C-Kit (BD Biosciences) antibodies. Then, Ep-CAM$^+$/C-Kit$^-$ HBs were sorted through flow cytometry. The sorted HBs were expanded and cultured in a plate coated with 1% Matrigel in optimized HB expansion medium $AB_{10}$CEHS, that is, basal medium RPMI1640 containing 2% of B27 and 1% of ITS (life), containing cytokines: 20 ng/mL of BMP4 and 20 ng/mL of EGF, and small molecule compounds: 20 ng/mL of HGF, 3 μM of CHIR, 5 μM of A8301, and 0.5 μM of SAG. Cells were digested with Accutase and subcultured when grown to 80% confluency.

Figure 3A:
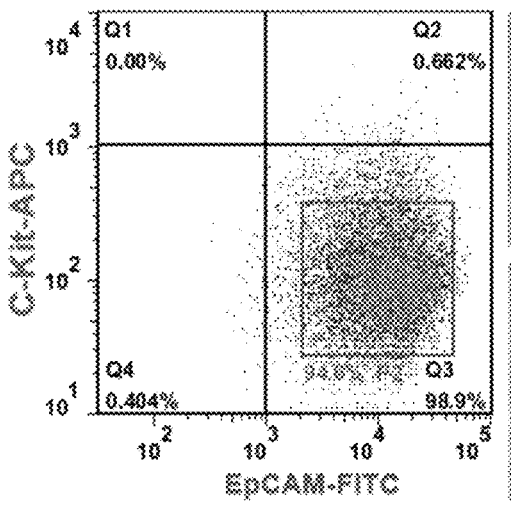
FIG. 3A illustrates purification of HBs obtained from hPSC induction through flow cytometry sorting according to the present application.
Figure 3B:
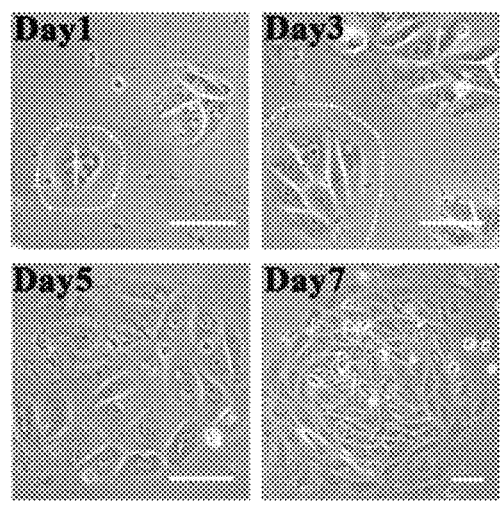
FIG. 3B is a diagram illustrating the capability of the sorted HBs to form clones under expansion and culture conditions according to the present application.
Figure 3C:
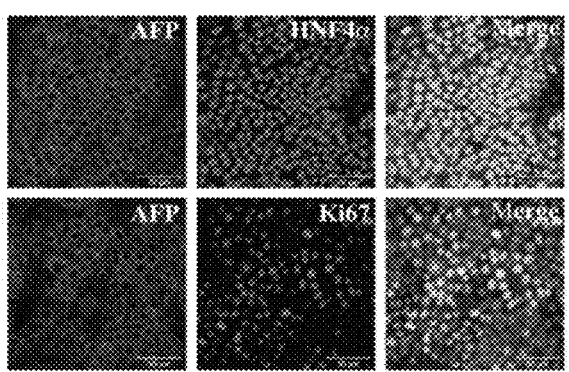
FIGS. 3C and 3D are diagrams illustrating that HBs expanded for a long term still maintained a relatively high capability of proliferation according to the present application.
Figure 3D:
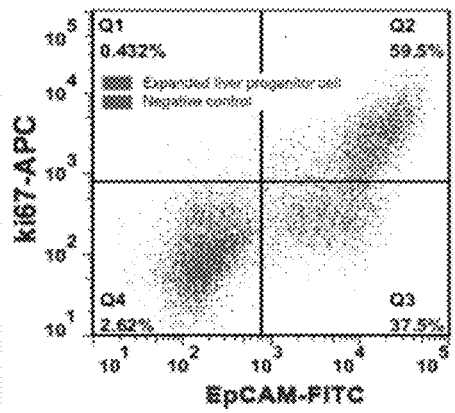
Figure 3E:
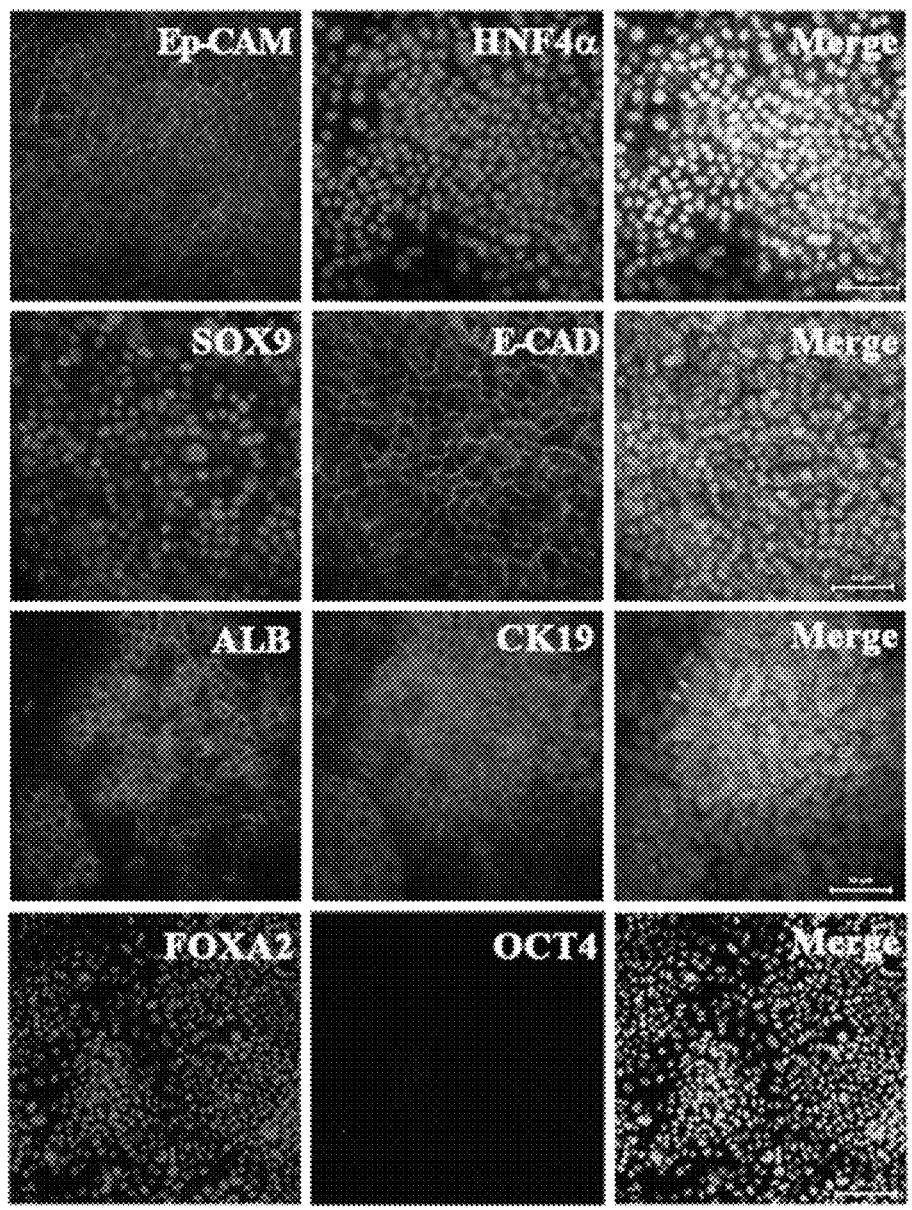
FIG. 3E is a diagram showing detected expression of marker proteins of HBs according to the present application.
Figure 3F:
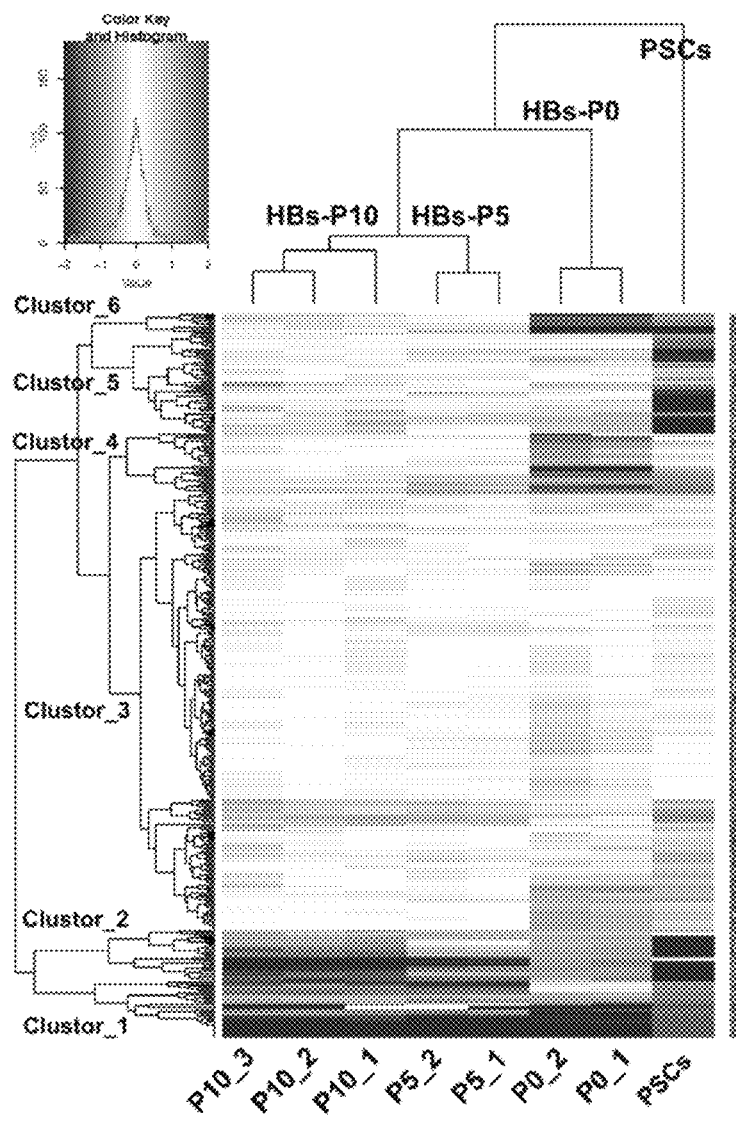
FIGS. 3F and 3G are diagrams showing results of analysis of HBs before and after expansion through a comparison of transcriptome according to the present application.
Figure 3G:
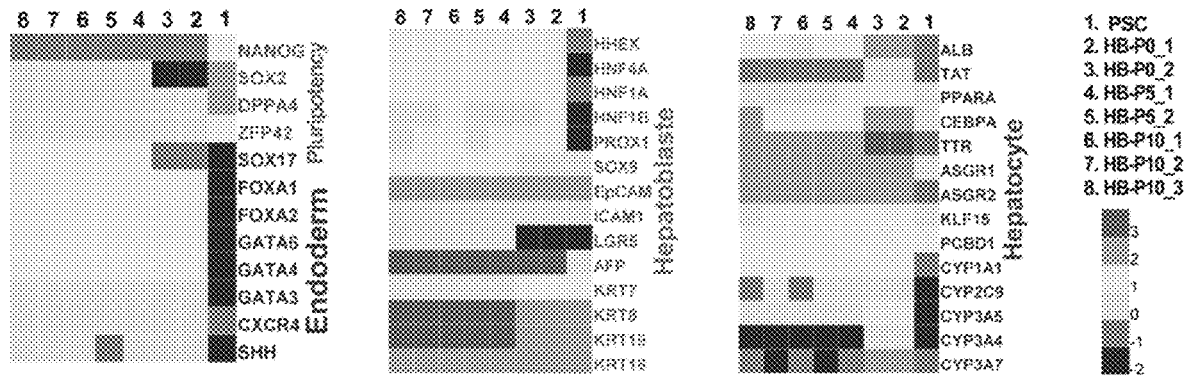

FIGS. 3A to 3G show the long-term expansion and identification of HBs, wherein: a diagram showing purification of HBs induced from hPSCs through flow cytometry sorting (FIG. 3A), a diagram illustrating the capability of the sorted HBs to form clones under expansion and culture conditions (FIG. 3B), diagrams illustrating that HBs expanded for a long term still maintained a relatively high capability to proliferate (FIGS. 3C and 3D), a diagram showing detected expression of marker proteins of HBs (FIG. 3E), and diagrams showing analysis of HBs before and after expansion through a comparison of transcriptome (FIGS. 3F and 3G).

As shown in FIGS. 3F and 3G, the expanded HBs expressed a series of marker proteins of HBs, such as AFP, HNF4, EpCAM, E-CAD, and SOX9. Meanwhile, the results of flow cytometry showed that nearly 60% of cells were positive for both Ki-67 and EpCAM, which indicates that HBs have a strong capability to proliferate. Under these culture conditions, HBs can be continuously expanded and cultured for more than 50 passages. The optimized liver expansion medium allows HBs to be expanded for a long term while maintaining their liver progenitor characteristics. The HBs expanded for a long term maintain a strong capability to proliferate.

The above results show that the system and method for expanding and culturing HBs, which are established in the present application, can selectively expand HBs obtained by inducing hPSCs for a long time while maintaining stable HB phenotypes and related functions.

Example 3 HBs Being Induced to Differentiate into Functional Mature Hepatocytes and Cholangiocytes HBs were grown to 90% confluency under expansion and culture conditions, then the culture medium was changed to a mature hepatocyte induction medium, that is, basal medium HepatoZYME-SFM (Gibco) containing 10 ng/mL of OncostatinM (OSM), 0.1 μM of dexamethasone (DEX; Sigma-Aldrich) and 0.5 mM of NH4Cl (Sigma-Aldrich). The HBs were induced for seven days and differentiated into hepatocyte-like cells.

Figure 4A:
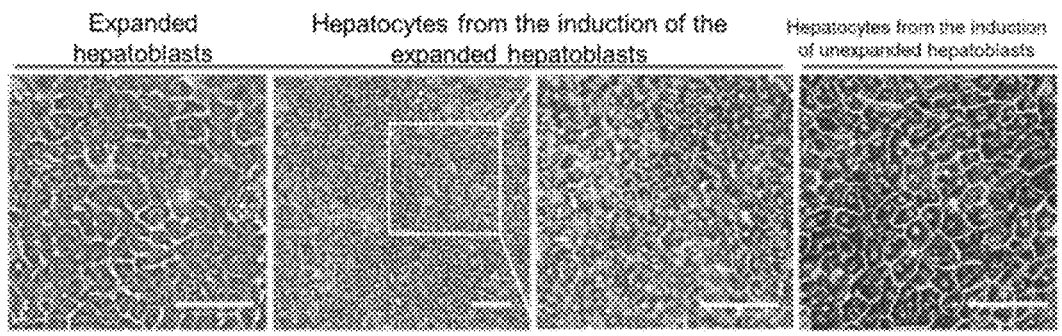
FIG. 4A is a morphology diagram of differentiation of expanded HBs into mature hepatocytes according to the present application.
Figure 4B:
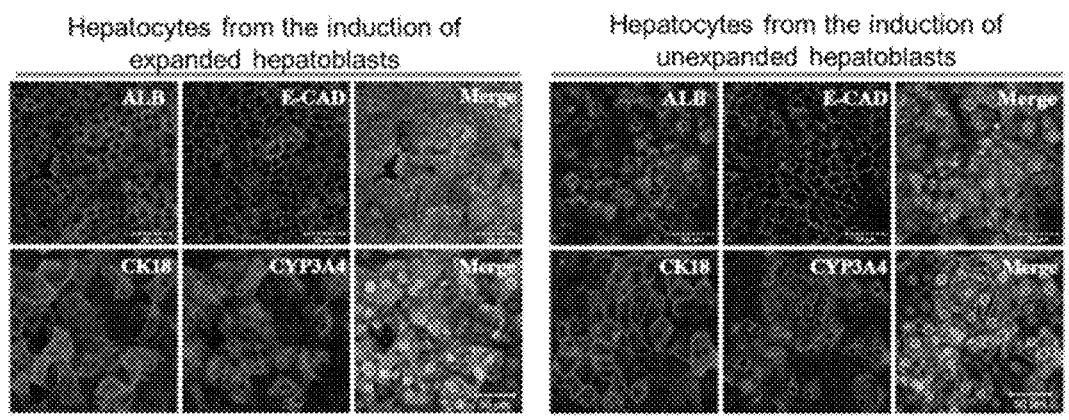
FIG. 4B is a diagram of differentiation of expanded HBs into hepatocytes that express marker proteins according to the present application.
Figure 4C:
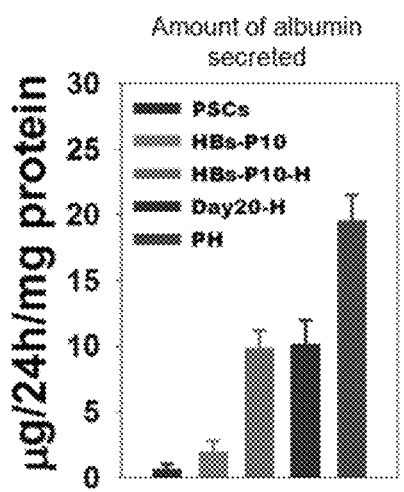
FIGS. 4C to 4F are diagrams illustrating identification of functions of hepatocytes obtained through induced differentiation which include metabolic detoxification and synthesis of albumin, urea, and glycogen according to the present application.
Figure 4D:
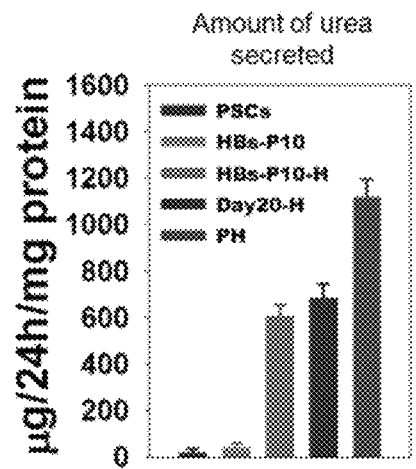
Figure 4E:
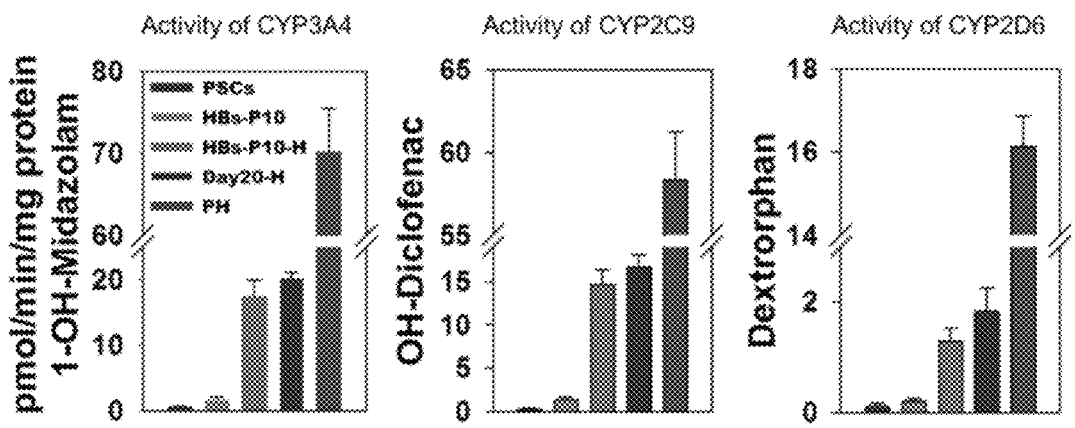
Figure 4F:
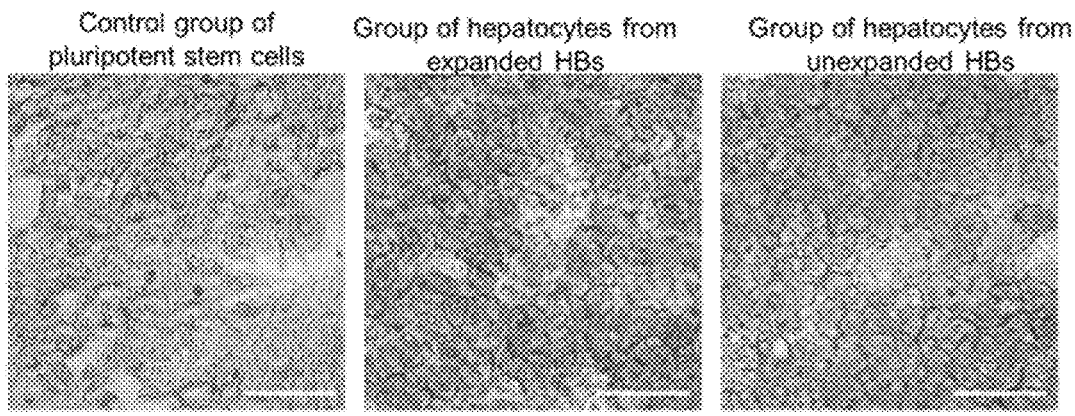
Figure 4G:
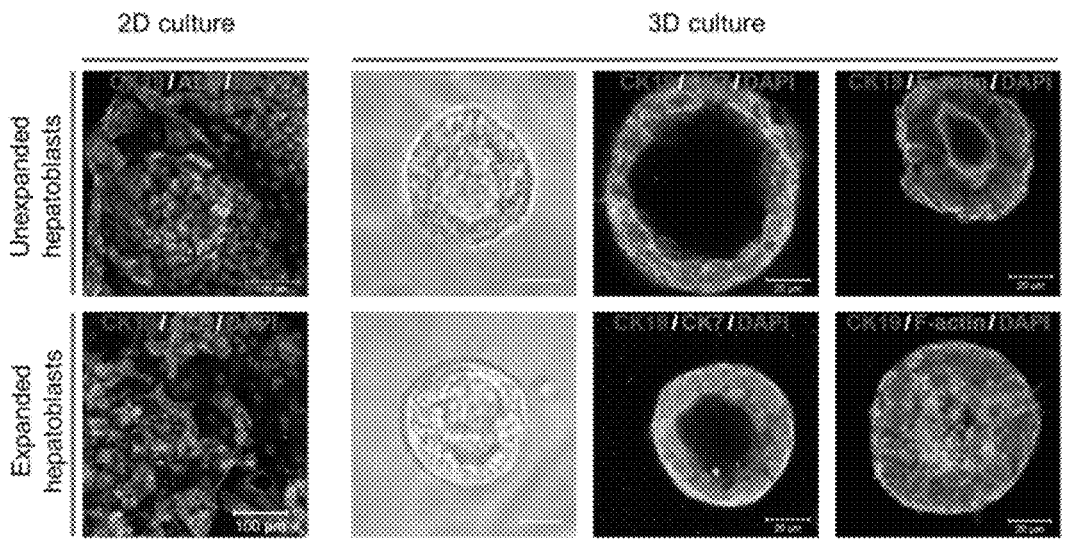
FIG. 4G is a diagram showing results of differentiation of HBs into bile duct epithelial cells and bile ducts according to the present application.

FIGS. 4A to 4G show that the expanded HBs maintained the dual potential to differentiate into hepatocytes and cholangiocytes. The expanded HBs were efficiently induced to differentiate into hepatocytes and expressed corresponding marker proteins ALB, CK18, HNF6, E-CAD, and CYP3A4 (FIGS. 4A and 4B). The hepatocytes obtained through induction of differentiation had strong functions of mature hepatocytes, such as metabolic detoxification and urea synthesis (FIGS. 4C and 4F). HBs were differentiated into bile duct epithelial cells (FIG. 4G). Effective differentiation of the expanded HBs into hepatocyte-like cells and cholangiocytes indicates that the long-term expansion does not affect the capability of HBs to differentiate. The hepatocytes obtained through induction of differentiation had strong functions of mature hepatocytes, such as metabolic detoxification and urea synthesis.

As shown in FIGS. 4A to 4G, HBs gradually transformed into square typical hepatocyte epithelioid morphology. Immunofluorescence results showed that the hepatocyte-like cells obtained through induction expressed multiple marker proteins of mature hepatocytes, such as ALB, CK18, HNF6, and CYP3A4. A further analysis of hepatocyte functions showed that the hepatocytes obtained through induction had typical functions of mature hepatocytes, such as albumin secretion, urea secretion, metabolism of substrates of CYP enzyme and glycogen synthesis.

These results show that the system and method for expanding and culturing HBs, which are established in the present application, can expand HBs for a long term without affecting their capability to differentiate, and the expanded HBs may be rapidly and efficiently induced to differentiate into mature hepatocytes with strong function of mature hepatocytes, such as metabolic detoxification and urea synthesis. The culture medium needs to be changed every day in the above cell culture and induction process.

Under Matrigel 3D culture conditions, both expanded and unexpanded HBs were differentiated into bile duct structures in a bile duct differentiation medium and expressed cholangiocyte marker proteins such as CK7 and CK19. These results suggest that the expanded HBs have the same dual potential to differentiate into hepatocytes and cholangiocytes as the unexpanded HBs. Unless specially noted, the cytokines used for cell culture and induction were purchased from PeproTech and the small molecule compounds were purchased from Selleck.

Example 4 Transplantation of Expanded HBs to Repair the Liver in Mouse Models of Acute Liver Injury Immunodeficient NSI mice were treated with DMN to establish an acute liver injury model. HBs before and after expansion were transplanted into the mouse models of liver injury to verify the proliferation and differentiation of the HBs before and after expansion as well as functions thereof to repair injured liver in vivo.

Figure 5A:
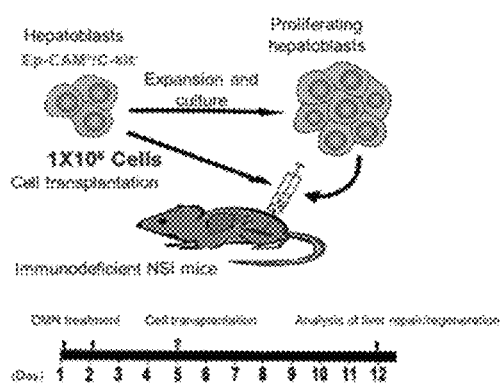
FIG. 5A is a schematic diagram of an HB transplantation experiment according to the present application.
Figure 5B:
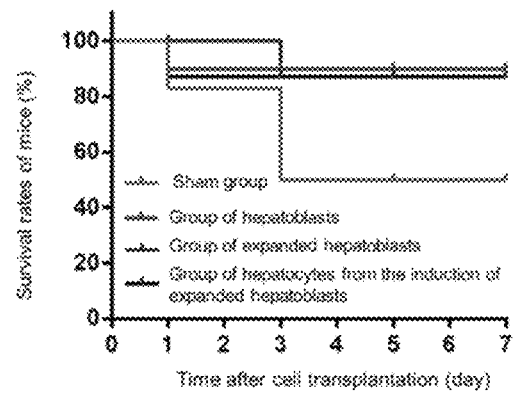
FIG. 5B is a diagram of an analysis of survival rates of animals before and after HB transplantation according to the present application.
Figure 5C:
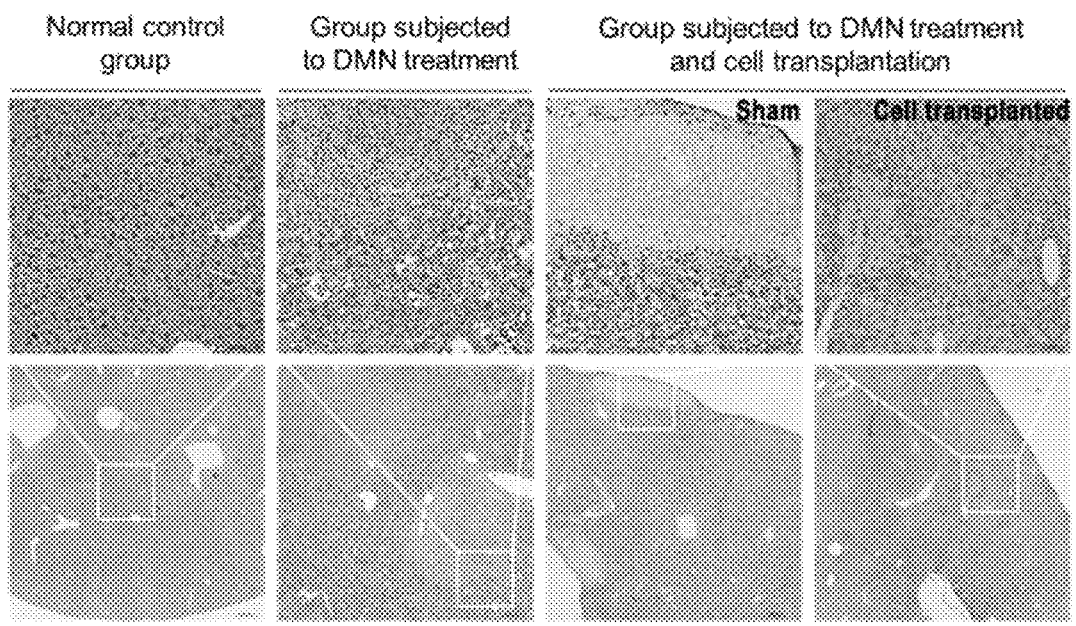
FIG. 5C is a diagram illustrating pathology sections for analyzing morphological structures of liver tissues before and after cell transplantation according to the present application.
Figure 5G:
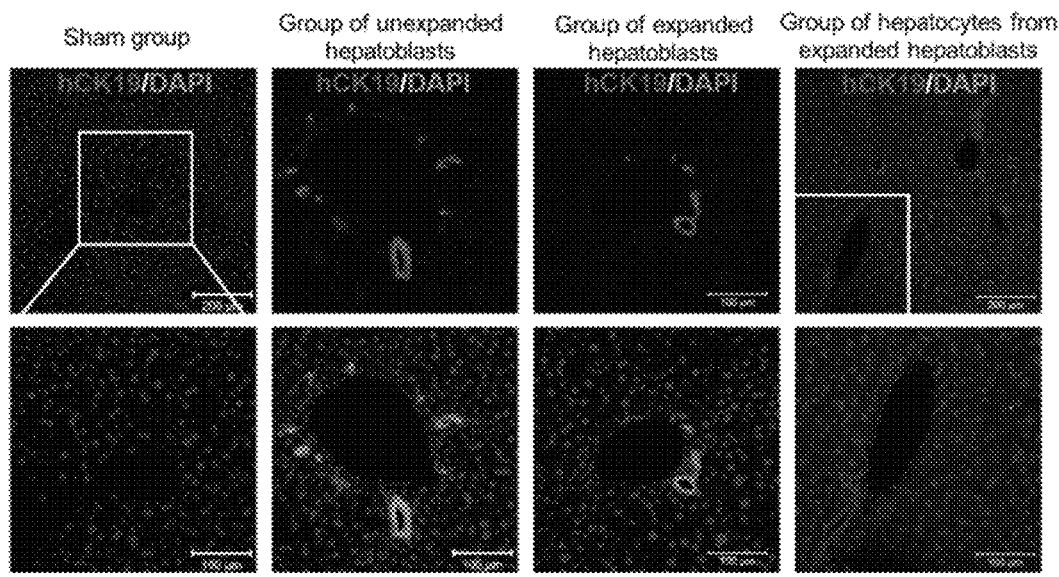
FIG. 5G is a diagram illustrating differentiation of transplanted HBs into bile duct epithelial cells to regenerate bile ducts according to the present application.
Figure 5H:
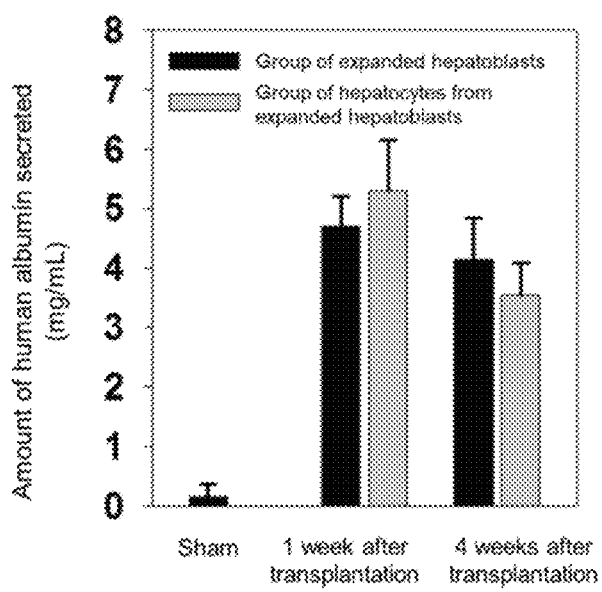
FIG. 5H is a diagram of secretion of human albumin in serum of mice transplanted with HBs according to the present application.
Figure 5I:
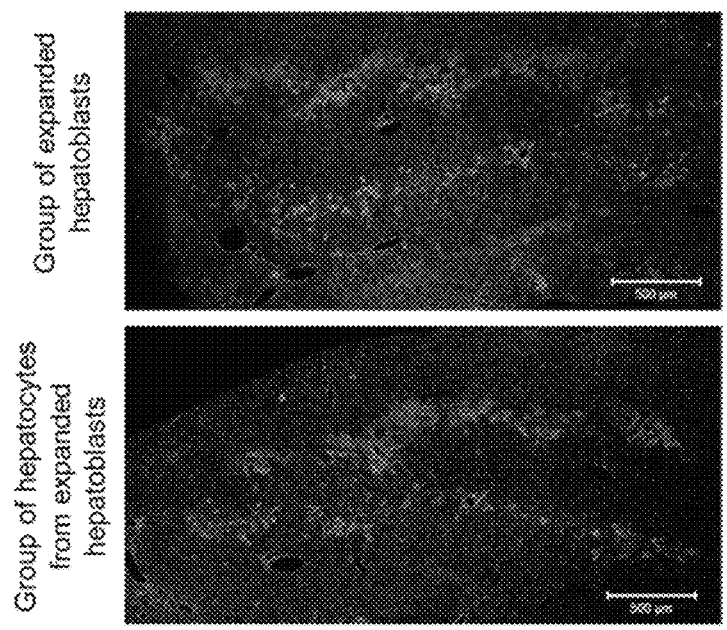
FIG. 5I is a diagram illustrating liver tissue sections for analyzing human hepatocytes after four weeks of cell transplantation according to the present application.

FIGS. 5A to 5I show diagrams of the transplantation of HBs to repair mouse models of liver injury, wherein: a schematic diagram illustrating an HB transplantation experiment (FIG. 5A), analysis of animal survival rates before and after HB transplantation (FIG. 5B), pathology sections for the analysis of the morphology of liver tissues before and after cell transplantation (FIG. 5C), liver tissue sections for the analysis of cell homing efficiency after one week of cell transplantation (FIGS. 5D to 5F), differentiation of the transplanted HBs into bile duct epithelial cells and regeneration bile ducts (FIG. 5G), detection of secretion of human albumin in the serum of mice transplanted with HBs (FIG. 5H), and liver tissue sections for the analysis of human-derived hepatocytes after four weeks of cell transplantation (FIG. 5I).

As shown by experimental results in FIGS. 5A to 5I, HBs before and after expansion were both homed and colonized in recipient liver after splenic transplantation; and the transplanted HBs were differentiated into hepatocytes expressing human ALB and bile duct epithelial cells expressing CK19, participated in the regeneration and repair of liver injury parenchyma and the regeneration and reconstruction of bile ducts, restored liver functions, and improved the survival rate of liver injury model mice.

These results show that when transplanted into the liver injury model mice, the HBs expanded and cultured for a long term through the system and method for expanding and culturing HBs, which are established in the present application, can be homed and colonized into injured liver tissues, participate in the repair of liver parenchyma and the reconstruction of bile ducts, effectively recover the function of the injured liver, and save liver injury model animals, just like HBs before expansion. Therefore, the present disclosure will facilitate the rapid and efficient acquisition of a large number of functional hepatocytes and is suitable for use in clinical hepatocyte transplantation and hepatocyte reactors in bioartificial liver.

To conclude, the present application provides a culture medium for expanding and culturing human hepatoblasts and use thereof. The culture medium is simple and reasonable in formula, clear in chemical composition, and serum-free, have components that cooperate with each other for synergy, and is used for expanding and culturing HBs in vitro for a long term and maintaining the stemness of HBs, conducive to the rapid and efficient acquisition of a large number of functional hepatocytes, and suitable for use in clinical hepatocyte transplantation and hepatocyte reactors in bioartificial liver. The present application will bring hope for the lives of millions of new liver cirrhosis patients at a compensation/decompensation stage and patients with acute hepatotoxicity and has a broad application prospect and a huge market value.

The applicant has stated that although the detailed method of the present application is described through the examples described above, the present application is not limited to the detailed method described above, which means that implementation of the present application does not necessarily depend on the detailed method described above. It should be apparent to those skilled in the art that any improvements made to the present application, equivalent replacements of raw materials of the product of the present application, additions of adjuvant ingredients to the product of the present application, and selections of specific manners, etc., all fall within the protection scope and the disclosed scope of the present application.

What is claimed is:

1. A culture medium for expanding and culturing human hepatoblasts, comprising:
    (a) a liquid basal culture medium,
    (b) an insulin-transferrin-sodium selenite mixture,
    (c) a cytokine,
    (d) a glycogen synthase kinase 3β inhibitor,
    (e) a Hedgehog signaling pathway activator, and
    (f) a transforming growth factor β receptor inhibitor.

2. The culture medium according to claim 1, further comprising albumin.

3. The culture medium according to claim 1, wherein the cytokine comprises a bone morphogenetic growth factor, hepatocyte growth factor, and epidermal growth factor.

4. The culture medium according to claim 1, wherein the glycogen synthase kinase 3β inhibitor has a concentration of 10 nM to 100 μM.

5. The culture medium according to claim 1, wherein the glycogen synthase kinase 3β inhibitor comprises CHIR99021 and/or CHIR98014;
    the transforming growth factor β receptor inhibitor comprises any one or a combination of at least two of A8301, SB431542, or E-616452;
    the Hedgehog signaling pathway activator comprises SAG and/or Purmorphaminede.

6. The culture medium according to claim 2, wherein the liquid basal culture medium comprises any one or a combination of at least two of a cell culture medium RPMI 1640, a cell culture medium DMEM/F 12, a cell culture medium MEM, a cell culture medium DMEM, a cell culture medium IMDM, a cell culture medium 199, or a cell culture medium F10.

7. The culture medium according to claim 2, wherein the albumin comprises human recombinant albumin and/or bovine serum albumin.

8. The culture medium according to claim 2, wherein the albumin has a mass concentration of 5 µg/mL to 500 µg/mL.

9. The culture medium according to claim 3, wherein the bone morphogenetic growth factor comprises BMP2 and/or BMP4.

10. The culture medium according to claim 3, wherein the bone morphogenetic growth factor has a mass concentration of 1 ng/ml to 50 ng/mL.

11. The culture medium according to claim 3, wherein the hepatocyte growth factor has a mass concentration of 1 ng/ml to 100 ng/mL.

12. The culture medium according to claim 3, wherein the epidermal growth factor has a mass concentration of 1 ng/ml to 200 ng/mL.

13. The culture medium according to claim 1, wherein the insulin-transferrin-sodium selenite mixture has a volume percent content of 0.1% to 10%.

14. The culture medium according to claim 1, wherein the transforming growth factor β receptor inhibitor has a molar concentration of 50 nM to 50 µM.

15. The culture medium according to claim 1, wherein the Hedgehog signaling pathway activator has a molar concentration of 10 nM to 50 µM.

16. A method for culturing and expanding human hepatoblasts in vitro, wherein the hepatoblasts are cultured in the medium of claim 1, comprising:
  a) obtaining Ep-CAM$^+$/C-kit$^+$ hepatoblasts, wherein the Ep-CAM$^+$/C-kit$^+$ hepatoblasts are from human pluripotent stem cells, hepatic stem cells, hepatoblasts or oval cells, and wherein the Ep-CAM$^+$/C-kit$^+$ hepatoblasts are obtained by flow cytometry cell sorting; and
  b) subculturing the hepatoblasts obtained in step (a).

* * * * *